United States Patent [19]

Izawa et al.

[11] 4,113,795
[45] Sep. 12, 1978

[54] FLAME-RETARDANT POLYPHENYLENE ETHER RESIN COMPOSITION

[75] Inventors: Shinichi Izawa, Tokyo; Jun Sugiyama; Tsutomu Tanaka, both of Yokohama; Atsuo Nakanishi, Kanagawa; Toranosuke Saito, Kobe, all of Japan

[73] Assignees: Asahi-Dow Limited, Tokyo; Sanko Kaihatsu Kagaku Kenkyusho, Osaka, both of Japan

[21] Appl. No.: 812,737

[22] Filed: Jul. 5, 1977

[51] Int. Cl.$^2$ ............................................. C08K 5/53
[52] U.S. Cl. ............................ 260/874; 260/45.8 R; 260/45.8 NT; 260/927 R; 260/936
[58] Field of Search ............... 260/45.8 R, 45.8 NT, 260/874, 927 R, 936

[56] References Cited

U.S. PATENT DOCUMENTS

| | | | |
|---|---|---|---|
| 3,702,878 | 11/1972 | Saito | 260/936 |
| 3,793,289 | 2/1974 | Koch et al. | 260/45.8 NT |
| 3,876,635 | 4/1975 | Deiner et al. | 260/830 R |
| 3,885,912 | 5/1975 | Golborn et al. | 8/116 P |
| 3,887,646 | 6/1975 | Yonemitsu et al. | 260/874 |
| 3,890,406 | 6/1975 | Matsunaga et al. | 260/874 |
| 3,906,136 | 9/1975 | Weil | 8/116 P |
| 3,981,841 | 9/1976 | Abolins et al. | 260/874 |
| 4,020,124 | 4/1977 | Abolins et al. | 260/874 |

*Primary Examiner*—Donald E. Czaja
*Assistant Examiner*—R. A. White
*Attorney, Agent, or Firm*—Cushman, Darby & Cushman

[57] ABSTRACT

Flame-retardant composition comprising (1) a novel organic phosphorous compound having a substituent of

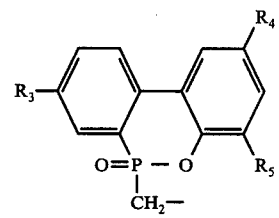

where $R_3$, $R_4$ and $R_5$ each is a monofunctional residue selected from a hydrogen atom, a halogen atom, an alkyl or aralkyl group having 1 to 8 carbon atoms, a cyclohexyl group and a phenyl group, on an amino group of an aromatic amino compound and (2) a mixture resin of polystyrene and polyphenylene ether grafted or not with a styrenic compound, said (1) being 2 – 20% by weight and (2) 80 – 98% by weight, on the basis of the composition.

40 Claims, No Drawings

FLAME-RETARDANT POLYPHENYLENE ETHER RESIN COMPOSITION

This invention relates to a flame-retardant polyphenylene ether resin composition. More particularly, the present invention relates to a flame-retardant resin composition having a novel organic phosphorus compound incorporated into a resin composition which has a styrenic polymer added to either a polyphenylene ether or a polyphenylene ether having graft copolymerized thereto a styrenic compound.

Polyphenylene ethers are excellent in mechanical properties, electrical properties, resistance to chemicals and thermal resistance and enjoy advantageous attributes such as low hydroscopicity and high dimensional stability. For the outstanding quality, they have been arresting keen attention. Further, polyphenylene ethers exhibit an excellent flame-retarding property such that they are rated as self-extinguishing and non-dripping by the Testing Method D-635 of ASTM and the Specification No. 94 of the Underwriter's Laboratories (hereinafter referred to UL-94). However, it has been long since deficient fabricability of polyphenylene ethers was pointed out. The poor fabricability has so far remained as the most serious defect for polyphenylene ethers. As measures for overcoming this defect, there have been suggested a number of methods resorting to incorporation of styrenic polymers. For example, Japanese Patent Publication No. 17812/1968, U.S. Pat. No. 3,383,435 and others have disclosed blended compositions of polyphenylene ethers with styrenic polymers. Resin compositions which contain graft copolymers having styrenic compounds grafted onto polyphenylene ethers have been disclosed in Japanese Patent Publication Nos. 1210/1972 and 27809/1971, Japanese Patent Laid-open Publication Nos. 98446/1974 and 51150/1974, U.S. Pat. Nos. 3,586,736 and 3,929,931 and others.

These resin compositions formulated to impart improved fabricability to polyphenylene ethers, however, have a disadvantage that they do not prove suitable for a wide range of industrial applications in terms of inflammability because styrenic polymers incorporated therein are resins of a type such that they are destitute of self-extinguishing property and non-dripping property and, once ignited, cannot but be left to burn out completely.

An object of the present invention is to provide polyphenylene ether resin compositions improved both in fabricability and flame-retardancy.

To be more specific, the present invention aims to provide a flame-retardant composition which is characterized by substantially comprising 80 to 98% by weight (based on the total composition) of a resin component obtained by mixing a styrenic polymer with either a polyphenylene ether or a polyphenylene ether having a styrenic compound with or without a vinyl compound copolymerizable therewith graft-copolymerized thereon, in such a proportion that the polyphenylene ether component represented by the generic formula:

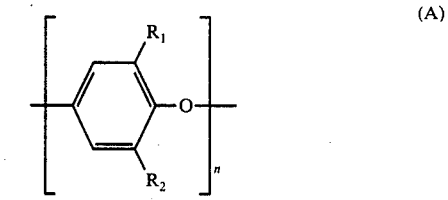

(wherein, $R_1$ and $R_2$ each denote an alkyl group having 1 to 4 carbon atoms and $n$ denotes the degree of polymerization) will account for 20 to 80% by weight (based on the total weight of resin component) and 2 to 20% by weight of at least one member selected from the group consisting of novel organic phosphorus compounds represented by the generic formulas:

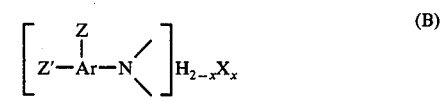

(wherein, Ar denotes a trifunctional aromatic residue, Z and Z' each denote a monofunctional residue selected from the class consisting of a hydrogen atom, an alkyl group having 1 to 4 carbon atoms, an aryl group having 6 to 10 carbon atoms and a $-NH_{2-y}X_y$ group, X denotes a residue of the formula

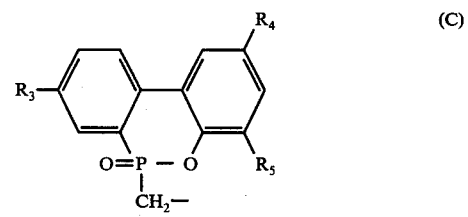

wherein $R_3$, $R_4$ and $R_5$ each denote a monofunctional residue selected from the class consisting of a hydrogen atom, a halogen atom, an alkyl having 1 to 8 carbon atoms, an aralkyl group, a cyclohexyl group and a phenyl group, $x$ denotes an integer having the value of 1 or 2 and $y$ denotes an integer having the value of 0, 1 or 2).

Examples of the aforementioned polyphenylene ethers used for the present invention include poly(2,6-dimethylphenylene-1,4-ether), poly(2,6-diethylphenylene-1,4-ether), poly(2-methyl-6-ethylphenylene-1,4-ether), poly(2-methyl-6-propylphenylene-1,4-ether), poly(2,6-dipropylphenylene-1,4-ether), poly(2-ethyl-6-propylphenylene-1,4-ether), poly(2-methyl-6-butylphenylene-1,4-ether) and poly(2-ethyl-6-butylphenylene-1,4-ether). The most advantageous polyphenylene ether for the purpose of the present invention is poly(2,6-dimethylphenylene-1,4-ether). This particular polymer excels in compatibility with styrenic polymers, permits resin compositions of varying proportions to be readily prepared and manifests an outstanding effect in imparting flame-retardancy due to its synergism with organic phosphorus compounds.

For the present invention to be effectively worked, the number-average molecular weight of a polyphenylene ether is selected from the range of 6,000 to 30,000, preferably 7,000 to 25,000. Use of a polyphenylene ether having a number-average molecular weight of less than 6,000 proves undesirable because the polymer notably degrades the resultant resin composition in physical properties, particularly creep properties. Use of a polyphenylene ether having a higher molecular weight exceeding 30,000 is likewise undesirable because the polymer seriously degrades the resin composition in fabricability, causes degradation of the styrenic polymer and inhibits maintenance of balanced physical properties.

In the polyphenylene ether having a styrenic compound graft-copolymerized thereon for use in the present invention, the term "styrenic compound" is meant to embrace styrene and various derivatives of styrene such as alkylation products and halogenation products of styrene. Concrete examples of styrene, α-methyl styrene, 2,4-dimethyl styrene, monochloro-styrene, dichloro-styrene, p-methyl styrene, ethyl styrene and the like.

At the time of polymerization, these styrenic compounds may be used in combination with 30% by weight or less of copolymerizable vinyl compounds such as, for example, methyl methacrylate, acrylonitrile, methacrylonitrile and butyl acrylate. Alternatively, the graft copolymerization may be effected by using two or more kinds of styrenic compounds at the same time.

The graft copolymer to be used in the resin composition of the present invention is desired to have 20 to 200 parts by weight of a styrenic compound with or without a vinyl compound copolymerizable therewith graft polymerized onto 100 parts by weight of a polyphenylene ether. If the amount of the styrenic compound with or without the vinyl comonomer is less than the lower limit 20 parts by weight, then the resultant graft copolymerized polyphenylene ether is substantially the same in quality as the polyphenylene ether in the form of a homopolymer. If the amount of the styrenic compound with or without the vinyl comonomer used in the graft polymerization exceeds the upper limit 200 parts by weight, then the styrenic compound with or without the vinyl comonomer degrades the physical properties, particularly, impact strength, of the resultant resin composition.

The term "styrenic polymer" as used in the present invention is meant to refer to a polymer formed preponderantly of a styrenic compound and possessed of a number-average molecular weight desirably in the range of from 50,000 to 200,000, preferably from 60,000 to 150,000. If the number-average molecular weight of the styrenic polymer is below 50,000, there is a disadvantage that the physical properties of the resultant resin, particularly impact strength and creep properties, are deficient. If it exceeds 200,000, however, there ensues and adverse effect upon the moldability and fabricability, which results in various undesirable phenomena such as thermal deterioration of the composition at the time of fabrication and impact resistance of the shaped article due to residual strain.

The term "styrenic compound" as used herein refers to the same compound as is used for the graft copolymerization described above. The styrenic polymers usable for this invention further include those commonly known rubber-reinforced styrenic resins. For example, rubber-reinforced polystyrene resins and acrylonitrile-butadiene-styrene copolymer resins are embraced in the scope of this invention. The proportion of the styrenic polymer to the total resin component of the composition (inclusive of the styrenic polymer which is chemically bonded to the polyphenylene ether in consequence of the graft copolymerization) is selected from the range of 20 to 80% by weight, preferably from 25 to 75% by weight. If the content of the styrenic polymer is less than the lower limit 20% by weight, the styrenic polymer fails to impart ample fabricability to the resultant resin composition. If the content exceeds the upper limit 80% by weight, it is difficult to confer desired flame-retardancy upon the resultant resin composition, even after by mixing with the organic phosphorus compound of the present invention.

Concrete examples of the trifunctional aromatic residue in the generic formula (B) are as follows:

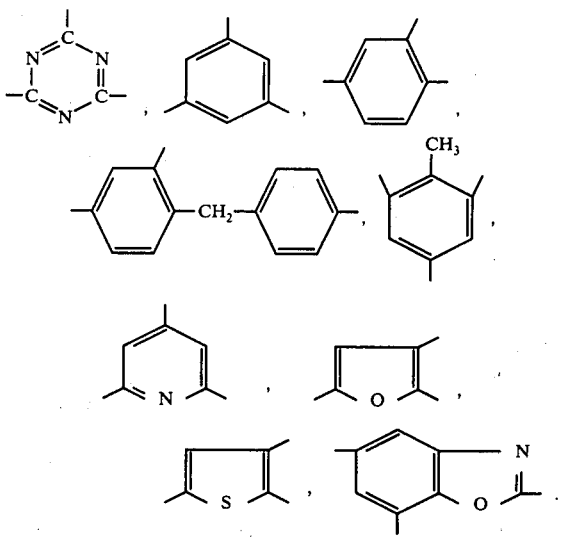

Concrete examples of the X component contained in the organic phosphorus compound represented by the generic formula (B) will be shown below in structural formula.

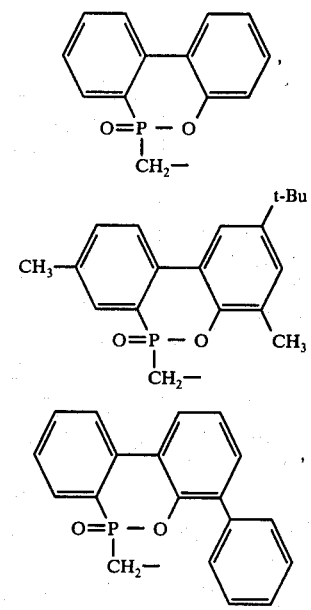

-continued

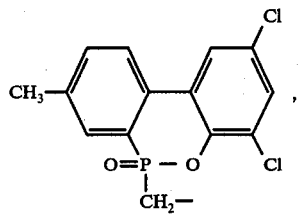

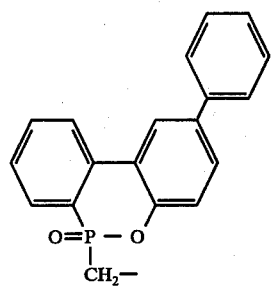

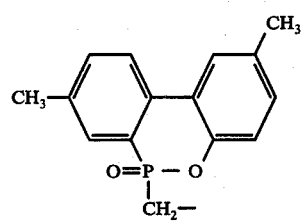

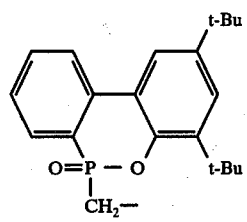

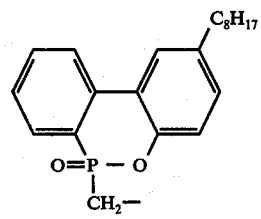

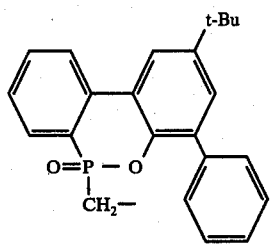

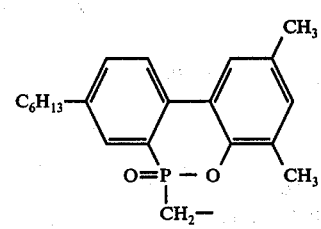

-continued

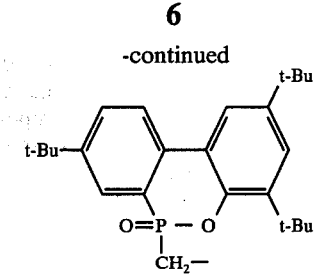

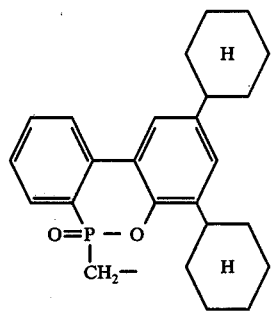

The compounds of the generic formula (B) are used either singly or in the form of a mixture consisting of two or more members.

The organic phosphorus compounds represented by the generic formula (B) (hereinafter called novel organic phosphorus compounds) which are usable for the present invention are novel ones that are obtained by a method in which organic phosphorus compounds represented by the generic formula:

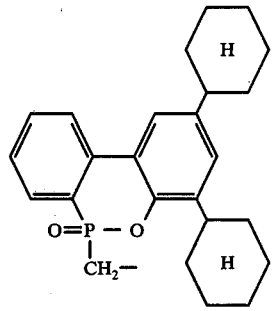

(wherein, $R_3$, $R_4$ and $R_5$ each denote a hydrogen atom, a halogen atom, an alkyl having 1 to 8 carbon atoms, an aralkyl group, a cyclohexyl group or a phenyl group) (refer to Japanese Patent Publication No. 17979/1975 in the Official Gazette) to dehydrogenation condensation in conjunction with an aromatic amino compound having amino groups directly bonded with aforementioned trifunctional aromatic residue. Alternatively, organic phosphorus compounds represented by the generic formula:

(wherein, $R_3$, $R_4$ and $R_5$ are as defined in the immediately preceding generic formula) (refer to Japanese Patent Publication No. 45397/1974 in the Official Gazette) may be subjected to dehydrogenation (or dealcohol) condensation in conjunction with an aromatic compound having methylolated amino groups directly bonded with the above trifunctional aromatic residue or said aromatic compound whose methylol groups are esterified.) Some of these compounds are disclosed under the title "organic phosphorus compounds" by the inventors in the specification of the patent application (Japanese Patent Application No. 78874/1976) filed under even date with the present patent application.

The novel organic phosphorus compound content required for manifestation of the effect of this invention is selected in the range of from 2 to 20%, preferably from 3 to 15%, by weight based on the total weight of the composition. If the content of the novel organic phosphorus compound is less than the lower limit 2%, there is an undesirable result that the resin composition will not easily acquire a quality capable of satisfying UL-94 tests for self-extinguishing property and non-dripping property. If the novel organic phosphorus compound is added in an amount greater than the upper limit 20%, then the resin composition has a disadvantage that its physical properties, particularly heat deflection temperature and impact strength, cannot be maintained in the ranges warranting practical utility.

The method to be used for the production of the composition of the present invention is not particularly limited, i.e. the components may be mixed by any method effective at all for the purpose. One typical example of the methods advantageously available comprises the steps of thoroughly mixing the resin destined to form the backbone of the final composition with the novel organic phosphorus compound in a dry blender, melting and kneading the mixture in an extruder and molding the molten mixture into pellets.

Needless to mention, it is permissible to incorporate in the composition of the present invention other additives such as, for example, a plasticizer, a pigment, a reinforcing agent a filler, an extender and a stabilizer as occasion demands.

Now, the present invention will be described more specifically with reference to examples thereof. Whenever there are mentioned parts and percents, they invariably mean parts by weight and percents by weight.

EXAMPLE 1

In a four-necked flask fitted with a stirrer and a thermometer, 77 parts of a phosphorus compound represented by the following formula and 29 parts of benzoguanamine were heated in an oil bath until the temperature within the flask rose to 170° C.

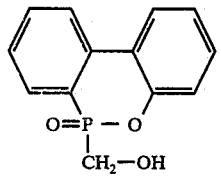

With the contents kept under agitation, the temperature was elevated to 230° C. over a period of 1 hour. Under a reduced pressure (30 mmHg of inner pressure), the water formed by the reaction was removed. When the reaction was continued for 2 hours at 230° C. under the reduced pressure, distillation of water ceased to proceed. At this point, the product of reaction was taken out of the flask, cooled and pulverized. The product was found to have a melting point of 128° C. The infrared absorption spectrum indicated decreases of OH group and $NH_2$ group. It was ascertained by the results of the elementary analysis that the reaction produced a novel organic phosphorus compound of the following formula

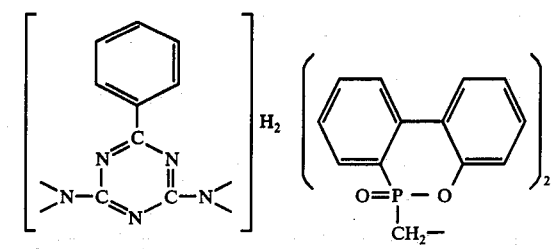

In a blender, 35 parts of poly(2,6-dimethylphenylene-1,4-ether) having a number-average molecular weight of 12,500, 65 parts of a rubber-reinforced styrene-acrylonitrile copolymer having an average acrylonitrile content of 4% and a styrene-butadiene copolymer rubber content of 9.0% and 8 parts of the novel organic phosphorus compound mentioned above were thoroughly mixed. Thereafter, the resultant mixture was melted and kneaded and molded into pellets by use of an extruder maintained at temperatures in the range of from 220° to 270° C. The mixed resin thus produced could be injection molded under conditions of 250° C. and 600 kg/cm². The molded product was found by tests to have a tensile strength of 440 kg/cm² (by the method of ASTM D638, which applies hereinafter), an Izod impact strength of 12.0 kg.cm/cm (by the method of ASTM D256, which applies hereinafter) and a heat deflection temperature of 88.2° C. (by the method of ASTM D648, which applies hereinafter). The mixed resin of this example was tested for inflammability by the method of UL-94. The ignition time was found to be 7.5 seconds at the most and 2.8 seconds on the average. In the creep test under tension which was performed at 23° C. under a load of 210 kg, the amount of creep after 1,000 hours of test was 0.99%.

EXAMPLE 2

In a blender, 60 parts of poly(2,6-dimethylphenylene-1,4-ether) having a number-average molecular weight of 21,000, 40 parts of a rubber-reinforced polystyrene containing 8% of polybutadiene rubber and 6 parts of the same novel organic phosphorus compound as used in Example 1 were mixed. The resultant mixture was melted and kneaded in an extruder kept at temperatures in the range of from 230° to 280° C., to produce pellets. The mixed resin thus produced could be injection molded under conditions of 260° C. and 700 kg/cm². It was found to have a tensile strength of 620 kg/cm², an Izod impact strength of 10.5 kg.cm/cm and a heat deflection temperature of 109.0° C. In the test for inflammability by the method of UL-94, the ignition time was found to be 5.5 seconds at most and 1.8 seconds on the average. Thus, the product was in the V-0 grade. In the creep tests under tension which were performed at 60° C. under a load of 105 kg and at 23° C. under a load of 210 kg, the amounts of creep after 1,000 hours were 0.58% and 1.01%, respectively.

EXAMPLE 3

In an extruder maintained at temperatures in the range of from 220° to 280° C., a resin component consisting of 65 parts of poly(2,6-dimethylphenylene-1,4- ether) having a number-average molecular weight of 9,500, 20 parts of a polystyrene-grafted polybutadiene having a polybutadiene content of 40% and 15 parts of a polystyrene having a number-average molecular weight of 105,000 was melted and kneaded and molded to produce a mixed resin in the form of pellets. In a blender, 100 parts of the pellets and 4.5 parts of the same novel organic phosphorus compound as used in Example 1 were mixed. The resultant mixture was melted and kneaded in an extruder kept at temperatures in the range of from 200° to 260° C. The resin composition thus produced could be injection molded under conditions of 240° C. and 450 kg/cm². It was found to have a tensile strength of 660 kg/cm², an Izod impact strength of 18.5 kg.cm/cm and a heat deflection temperature of 120° C. In the test for inflammability by the method of UL-94, the ignition time was 4.2 second at most and 2.6 seconds on the average. Thus, the product was in the V-0 grade. In the creep tests under tension performed at 60° C. under a load of 105 kg and at 23° C. under a load of 210 kg, the amounts of creep were 0.51% and 0.83% respectively, after 1,000 hours.

EXAMPLE 4

The procedure of Example 1 for the preparation of the organic phosphorus compound was repeated, except 99 parts of a phosphorus compound of the formula

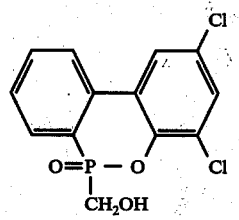

was used in place of

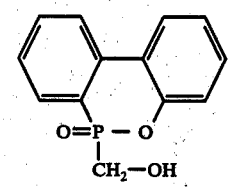

It was confirmed by the infrared absorption spectrum and the results of elementary analysis that the reaction produced an novel organic phosphorus compound of the following formula:

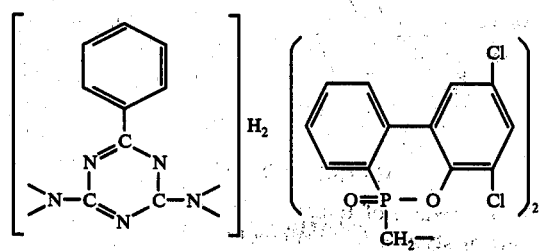

In a blender, 5 parts of this novel organic phosphorus compound and 100 parts of the mixed resin pellets obtained in Example 3 were thoroughly mixed. The resultant mixture was melted and kneaded in an extruder. The resin composition thus produced could be injection molded under conditions of 240° C. and 500 kg/cm². It was found to have a tensile strength of 590 kg/cm², an Izod impact strength of 16.8 kg.cm/cm and a heat deflection temperature of 116.5° C. In the inflammability test by the method of UL-94, the ignition time was 3.5 seconds at most and 1.6 seconds on the average. Thus, the product was in the V-0 grade.

REFERENCE EXAMPLE 1

This example involved use of an organic phosphorus compound which had not undergone the reaction with an amino group-containing compound to illustrate, through comparison of the results with those of Example 4, how much the omission of said reaction affected the heat deflection temperature.

In a blender, 100 parts of the mixed resin pellets obtained in Example 3 and 5 parts of an organic phosphorus compound represented by the following formula were thoroughly mixed and then melted and kneaded in an extruder. The resin composition thus produced could be injection molded under conditions of 280° C. and 550 kg/cm².

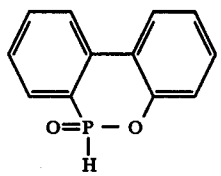

It was found to have a tensile strength of 590 kg/cm², an Izod impact strength of 11.8 kg.cm/cm and a heat deflection temperature of 109.5° C. In the inflammability test by the method of UL-94, the ignition time was 7.4 seconds at most and 3.1 seconds on the average. Thus, the product was in the V-0 grade.

EXAMPLE 5

Under continued agitation, 50 parts of poly(2,6-dimethylphenylene-1,4-ether) having a number-average molecular weight of 9,700, 20 parts of styrene and 1.0 part of di-t-butyl peroxide were heated to 150° C. over a period of 10 minutes and then to 240° C. over the following period of 10 minutes. The reaction product was molded into pellets by use of an extruder. The graft copolymer thus produced was found to have a polystyrene content of 26%. In 40 ml of methylene chloride, 2.0 g of the polymer was dissolved and was left to stand at 30° C. Even after 6 hours of this standing, absolutely no precipitation was recognized. This proves that no homopolymer of polyphenylene ether remained in the graft copolymer.

In a blender, a mixture consisting of 50 parts of this graft copolymer, 20 parts of a polystyrene-grafted polybutadiene having a polybutadiene content of 40% and 30 parts of a polystyrene having a number-average molecular weight of 88,000 was thoroughly mixed with 5.0 parts of the same novel organic phosphorus compound as used in Example 1. The resultant mixture was melted and kneaded in an extruder kept at temperatures in the range of from 200° to 260° C. The resin composition thus produced could be injection molded under conditions of 220° C. and 450 kg/cm². It was found to have a tensile strength of 430 kg/cm², an Izod impact strength of 22.5 kg.cm/cm and a heat deflection temperature of 106.5° C. In the test for inflammability performed by the method of UL-94, the ignition time was found to be 8.8 seconds at most and 4.2 seconds on the average. Thus the product was in the V-0 grade.

EXAMPLE 6

In a blender, 60 parts of the graft copolymer obtained in Example 5, 30 parts of a rubber-reinforced polystyrene having a polybutadiene rubber content of 8%, 10 parts of a polystyrene-grafted polybutadiene having a polybutadiene content of 40% and 3.5 parts of the same novel organic phosphorus compound as used in Example 4 were thoroughly mixed. In an extruder kept at temperatures in the range of from 200° to 260° C., the resultant mixture was melted and kneaded. The resin composition thus produced could be injection molded under conditions of 230° C. and 450 kg/cm². It was found to have a tensile strength of 460 kg/cm², an Izod impact strength of 23.0 kg.cm/cm and a heat deflection temperature of 112° C. In the test for inflammability performed by the method of UL-94, the ignition time was found to be 11.8 seconds at most and 6.8 seconds on the average. Thus, the product was in the V-1 grade.

EXAMPLES 7-10

By following the procedure of Example 1, novel organic phosphorus compounds were prepared by using not the phosphorus compound

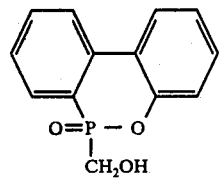

itself but its derivatives. By following the procedure of Example 4, the compounds were converted into resin compositions. These compositions were tested for inflammability by the method of UL-94. The results are shown collectively in Table 1.

Table 1

| Example No. | Organic phosphorus compound used | Test of resin composition for inflammability by the method of UL-94 | | |
|---|---|---|---|---|
| | | Maximum (seconds) | Average (seconds) | Rating |
| 7 | 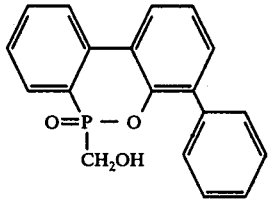 | 9.2 | 4.5 | V-0 |
| 8 | 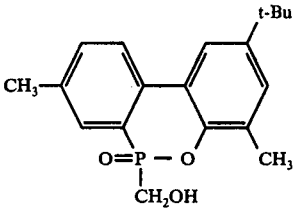 | 10.3 | 4.3 | V-1 |
| 9 | 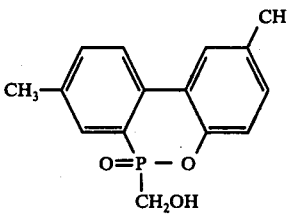 | 7.4 | 4.4 | V-0 |
| 10 | 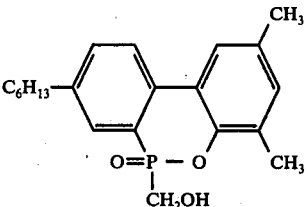 | 11.2 | 4.9 | V-1 |

EXAMPLES 11-13

The procedure of Example 5 was repeated with the amount of styrene for graft polymerization varied, to produce resin compositions. The compositions were tested for inflammability. The results are collectively shown in Table 2.

Table 2

| Ex. No. | Amount of polystyrene in graft copolymer (%) | Test of resin composition for inflammability by the method of UL-94 | | |
|---|---|---|---|---|
| | | Maximum (seconds) | Average (seconds) | Rating |
| 11 | 34 | 13.5 | 8.4 | V-1 |
| 12 | 45 | 20.2 | 12.6 | V-1 |
| 13 | 58 | 24.4 | 20.8 | V-1 |

EXAMPLES 14–18

The procedure of Example 6 was repeated with the added amount of the novel organic phosphorus compound varied. The resin compositions obtained consequently were tested for inflammability. The results are collectively shown in Table 3.

Table 3

| Ex. No. | Amount of organic phosphorus compound added (parts) | Test of resin composition for inflammability by the method of UL-94 | | |
|---|---|---|---|---|
| | | Maximum (seconds) | Average (seconds) | Rating |
| 14 | 2.5 | 20.5 | 14.6 | V-1 |
| 15 | 4.5 | 10.1 | 4.8 | V-1 |
| 16 | 9 | 4.0 | 2.5 | V-0 |
| 17 | 13 | 3.5 | 1.4 | V-0 |
| 18 | 18 | 1.9 | 0.9 | V-0 |

EXAMPLE 19

A novel organic phosphorus compound was synthesized by repeating the procedure of Example 1, except 9.7 parts of melamine was used in place of the benzoguanamine. The product showed a melting point of 137° C. The infrared absorption spectrum indicated decreases of OH group and NH$_2$ group. It was confirmed by the results of the elementary analysis that the reaction produced a novel organic phosphorus compound of the following formula.

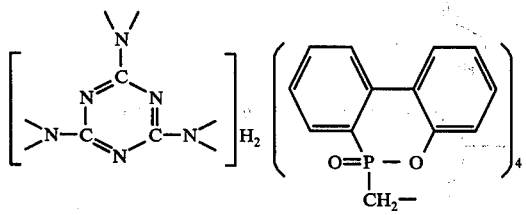

In a blender, 4.0 parts of this novel organic phosphorus compound was thoroughly mixed with 100 parts of pellets of the mixed resin obtained in Example 3. The resultant mixture was melted and kneaded in an extruder kept at temperatures in the range of from 200° to 260° C. The resin composition thus produced could be injection molded under conditions of 240° C. and 450 kg/cm$^2$. It was found to have a tensile strength of 620 kg/cm$^2$, an Izod impact strength of 19.2 kg.cm/cm and a heat deflection temperature of 121° C. In the test for inflammability conducted by the method of UL-94, the ignition time was 10.6 seconds at most and 4.1 seconds on the average. Thus, the product was in the V-1 grade.

EXAMPLE 20

In a four-necked flask fitted with a stirrer and a thermometer, 85 parts of a phosphorus compound represented by the following formula

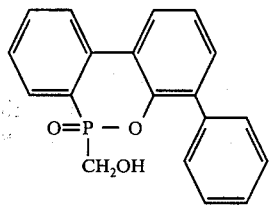

and 15 parts of methaphenylene diamine were heated in an oil bath until the temperature within the flask rose to 180° C. Under continued agitation, the temperature was further raised to 230° C. over a period of 1 hour, during which period the formed water was removed under reduced pressure (interior pressure 40 mmHg). When the reaction was continued at 230° C. under said reduced pressure for 2 hours, distillation of water ceased to occur. At this time, the product was taken out of the flask, cooled and pulverized. It showed a melting point of 119° C. It was confirmed by the results of the infrared absorption spectrum and the elementary analysis that the reaction produced a novel organic phosphorus compound of the following formula:

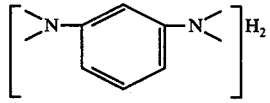

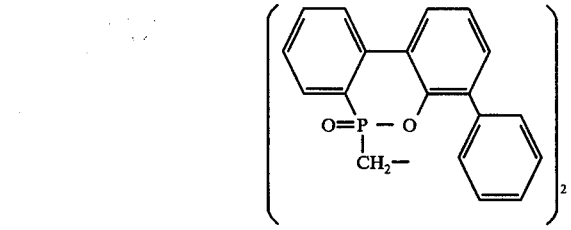

A thorough mixture of 65 parts of poly(2,6-dimethylphenylene-1,4-ether) having a number-average molecular weight of 18,000, 15 parts of styrene and 1.0 part of di-t-butyl peroxide was passed through an extruder kept at temperatures in the range of from 190° to 230° C. to undergo polymerization and pelletization at the same time. The graft copolymer thus obtained was found to have a polystyrene content of 17.7%. When a 2.0-g portion of the polymer was dissolved in 40 ml of methylene chloride and the solution was left to stand at 30° C. overnight, absolutely no precipitate was found. This proves that no homopolymer of polyphenylene ether remained in the graft copolymer.

In a blender, a resin component consisting of 50 parts of this graft copolymer, 20 parts of a styrene-grafted polybutadiene having a polybutadiene content of 40% and 30 parts of a polystyrene having a number-average molecular weight of 85,000 was thoroughly mixed with 6 parts of the novel organic phosphorus compound of which the method of preparation has been indicated in this example. The resultant mixture was melted and kneaded in an extruder kept at temperatures in the range of from 200° to 240° C. The resin composition thus produced could be injection molded under conditions of 220° C. and 450 kg/cm$^2$. It was found to have a tensile strength of 440 kg/cm$^2$, an Izod impact strength of 18.5 kg.cm/cm and a heat deflection temperature of 107° C. In the test for inflammability performed by the method of UL-94, the ignition time was found to be 7.5 second at most and 3.9 seconds on the average. Thus, the product was in the V-0 grade.

EXAMPLE 21

In a four-necked flask fitted with a stirrer and a thermometer, 72 parts of a phosphorus compound represented by the following formula:

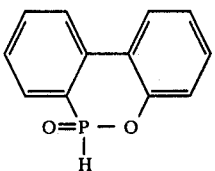

and 28 parts of bis(methoxymethyl)-paraphenylenediamine were heated in an oil bath until the temperature within the flask rose to 160° C. Under continued agitation, the temperature was further raised to 220° C. over a period of 1 hour, during which period the reaction was continued removing the formed methanol under a reduced pressure (interior pressure 30 mmHg). The interior temperature was raised up to 250° C. After the distillation of methanol ceased to proceed, the product was taken out of the flask, cooled and finely pulverized. This product showed a melting point of 152° C. It was confirmed from the results of the infrared absorption spectrum and the elementary analysis that the reaction produced a novel organic phosphorus compound of the following formula:

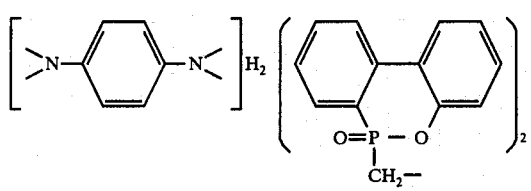

In a blender, 3.5 parts of this novel organic phosphorus compound, 70 parts of the styrene-grafted polyphenylene ether obtained in Example 20. 20 parts of a styrene-grafted polybutadiene having a polybutadiene content of 40% and 10 parts of a polystyrene having a number-average molecular weight of 92,000 were thoroughly mixed. The resultant mixture was melted and kneaded in an extruder kept at temperatures in the range of from 210° to 260° C. The resin composition thus produced could be injection molded under conditions of 240° C. and 550 kg/cm². It was found to have a tensile strength of 520 kg/cm², an Izod impact strength of 23.5 kg.cm/cm and a heat deflection temperature of 224° C. In the test for inflammability performed by the method of UL-94, the ignition time was found to be 6.5 seconds at most and 3.8 seconds on the average. Thus, the product was in the V-0 grade.

EXAMPLES 22–24

The procedure of Example 21 was repeated, except the aromatic amino compound derivatives shown in Table 4 were used in place of bis(methoxymethyl)-paraphenylenediamine.

The results of the inflammability test conducted on the resultant resin compositions by the method of UL-94 are shown in the following table.

Table 4

| Example No. | Aromatic amino compound derivative used | Test of resin composition for inflammability by the method of UL-94 | | |
|---|---|---|---|---|
| | | Maximum (seconds) | Average (seconds) | Rating |
| 22 | (CH₃OCH₂NH—⟨phenyl⟩)₂—CH₂ | 7.2 | 4.5 | V-0 |
| 23 | CH₃OCH₂NH—⟨phenyl with CH₃, NHCH₂OCH₃, NHCH₂OCH₃⟩ | 5.0 | 2.9 | V-0 |
| 24 | NHCH₂OC₄H₉ biphenyl NHCH₂OC₄H₉ | 9.2 | 5.1 | V-1 |

EXAMPLES 25–27

The procedure of Example 20 was repeated, except the diamines shown in Table 5 were used in place of methaphenylene diamine. The results of the test performed on the resultant resin compositions for inflammability by the method of UL-94 are shown in the following table.

Table 5

| Example No. | Diamine used | Test of resin composition for inflammability by the method of UL-94 | | |
|---|---|---|---|---|
| | | Maximum (seconds) | Average (seconds) | Rating |
| 25 | ![diamine with CH3 and two NH2] | 8.6 | 4.6 | V-0 |
| 26 | H₂N—pyridine—NH₂ | 5.2 | 4.1 | V-0 |
| 27 | H₂N—thiophene—NH₂ | 9.1 | 5.2 | V-1 |

EXAMPLE 28-31

The procedure of Example 21 was repeated, except varying combinations of phosphorus compounds and aromatic amino compound derivatives were used. The resultant resin compositions were tested for strengths and for inflammability by UL-94. The results are collectively shown in Table 6.

polyphenylene ether represented by the generic formula:

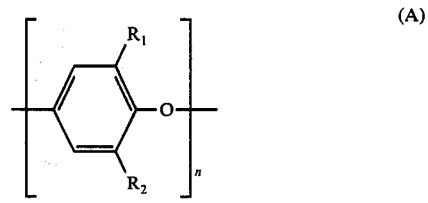

(A)

(wherein, $R_1$ and $R_2$ each denote an alkyl group having 1 to 4 carbon atoms and $n$ denotes the degree of polymerization) and 20 to 80% by weight of a styrenic polymer and 2 to 20% by weight of at least one member selected from the group consisting of organic phosphorus compounds represented by the generic formula:

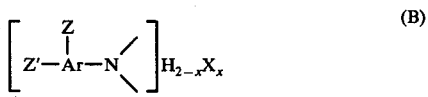

(B)

(wherein, Ar denotes a trifunctional residue of the formula:

Table 6

| Example No. | Organic phosphorus compound used | Aromatic amino compound derivative used | Tensile strength (kg/cm²) | Izod impact strength (kg.cm/cm) | Test of resin composition for: Inflammability by UL-94 | | |
|---|---|---|---|---|---|---|---|
| | | | | | Maximum (seconds) | Average (seconds) | Rating |
| 28 | biphenyl with Cl substituents, O=P—O—H | CH₃OCH₂NH—furan—NHCH₂OCH₃ | 510 | 20.5 | 4.1 | 2.7 | V-0 |
| 29 | biphenyl with t-Bu substituents, O=P—O—H | CH₃OCH₂NH—benzene with two NHCH₂OCH₃ | 525 | 19.8 | 11.5 | 6.2 | V-1 |
| 30 | biphenyl with CH₃ and t-Bu substituents, O=P—O—H | CH₃OCH₂NH—benzene—NHCH₂OCH₃ | 530 | 22.0 | 9.2 | 5.3 | V-1 |
| 31 | biphenyl with Cl substituents, O=P—O—H | CH₃OCH₂NH—benzoxazole—NHCH₂OCH₃, NHCH₂OCH₃ | 510 | 22.5 | 4.8 | 2.9 | V-0 |

What we claim is:

1. A flame-retardant polyphenylene ether resin composition, substantially comprising 80 to 98% by weight of a mixed resin consisting of 20 to 80% by weight of a

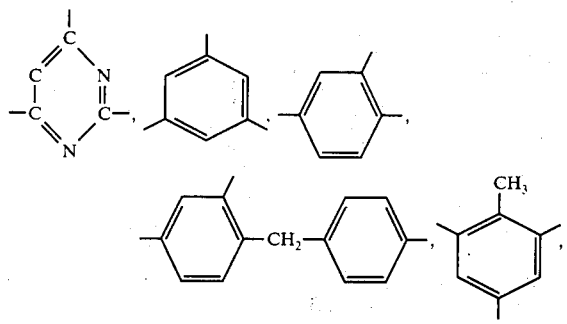

and Z and Z' each denote a monofunctional residue selected from the class consisting of a hydrogen atom, an alkyl group having 1 to 4 carbon atoms, an aryl group having 6 to 10 carbon atoms and a —NH$_{2-y}$X$_y$ group, X denotes a residue of the formula

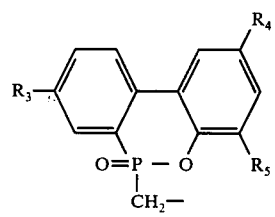

wherein, R$_3$, R$_4$ and R$_5$ each denote a monofunctional residue selected from the class consisting of a hydrogen atom, a halogen atom, an alkyl having 1 to 8 carbon atoms, an aralkyl group, a cyclohexyl group and a phenyl group, x denotes an integer having the value of 1 or 2 and y denotes an integer having the value of 0, 1 or 2).

2. The resin composition according to claim 1, wherein the residue (C) is such that all R$_3$, R$_4$ and R$_5$ each are a hydrogen atom.

3. The resin composition according to claim 1, wherein the residue (C) is such that R$_4$ and R$_5$ each are a chlorine atom and R$_3$ is a hydrogen atom.

4. The resin composition according to claim 1, wherein the residue (C) is such that all R$_3$, R$_4$ and R$_5$ each are a t-butyl group.

5. The resin composition according to claim 1, wherein the residue (C) is such that R$_5$ is a phenyl group and R$_3$ and R$_4$ each are a hydrogen atom.

6. The resin composition according to claim 1, wherein the residue (C) is such that R$_3$ and R$_5$ each are a methyl group and R$_4$ is a t-butyl group.

7. The resin composition according to claim 1, wherein the organic phosphorus compound (B) is such that Ar is a group of the formula

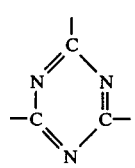

and Z and Z' each are a —NH$_{2-y}$X$_y$ group.

8. The resin composition according to claim 1, wherein the organic phosphorus compound (B) is such that Ar is a group of the formula

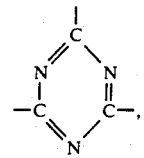

Z is a phenyl group and Z' is —NH$_{2-y}$X$_y$ group.

9. The resin composition according to claim 1, wherein the organic phosphorus compound (B) is such that Ar is a

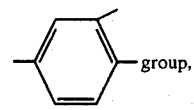

Z is a hydrogen atom and Z' is a —NH$_{2-y}$X$_y$ group.

10. The resin composition according to claim 1, wherein the organic phosphorus compound (B) is such that Ar is a

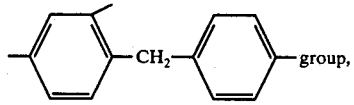

Z is a hydrogen atom and Z' is a —NH$_{2-y}$X$_y$ group.

11. The resin composition according to claim 1, wherein the organic phosphorus compound (B) is such that Ar is a

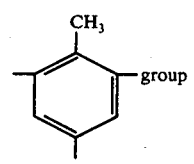

and Z and Z' each are a —NH$_{2-y}$X$_y$ group.

12. The resin composition according to claim 1, wherein the organic phosphorus compound (B) is such that Ar is a

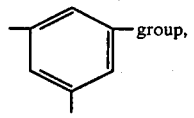

Z is a phenyl group and Z' is a —NH$_{2-y}$X$_y$ group.

13. The resin composition according to claim 1, wherein the organic phosphorus compound (B) is such that Ar is a

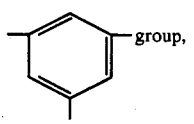

Z is a methyl group and Z' is a —NH$_{2-y}$X$_y$ group.

14. The resin composition according to claim 1, wherein the organic phosphorus compound (B) is such that Ar is a

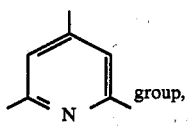 group,

Z is a hydrogen atom and Z' is a —NH$_{2-y}$X$_y$ group.

15. The resin composition according to claim 1, wherein the organic phosphorus compound (B) is such that Ar is a

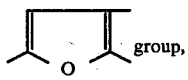 group,

Z is a hydrogen atom and Z' is a —NH$_{2-y}$X$_y$ group.

16. The resin composition according to claim 1, wherein the organic phosphorus compound (B) is such that Ar is a

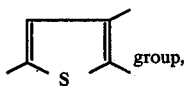 group,

Z is a hydrogen atom and Z' is a —NH$_{2-y}$X$_y$ group.

17. The resin composition according to claim 1, wherein the organic phosphorus compound (B) is such that Ar is a

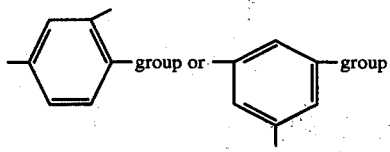

and Z and Z' each are a phenyl group.

18. The resin composition according to claim 1, wherein the organic phosphorus compound (B) is such that Ar is a

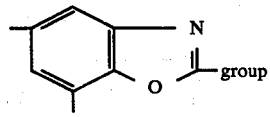

and Z' is a —NH$_{2-y}$X$_y$ group.

19. The resin composition according to claim 1, wherein the organic phosphorus compound to be used is a mixture consisting of organic phosphorus compounds of the formula (B) wherein x is 1 or 2 and y is 0, 1 or 2.

20. The resin composition according to claim 1, wherein the polyphenylene ether (A) is such that R$_1$ and R$_2$ each are a methyl group.

21. A flame-retardant polyphenylene ether resin composition, substantially comprising 80 to 98% by weight of a resin component and 2 to 20% by weight of at least one member selected from the group of organic phosphorus compounds represented by the generic formula:

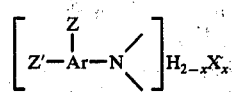

(wherein, Ar denotes a trifunctional residue of the formula

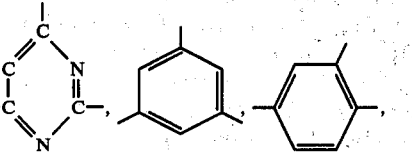

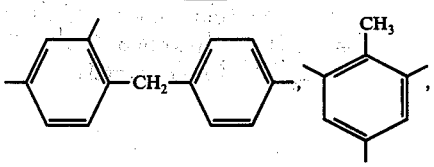

Z and Z' each denote a monofunctional residue selected from the class consisting of a hydrogen atom, an alkyl group having 1 to 4 carbon atoms, an aryl group having 6 to 10 carbon atoms and a —NH$_{2-y}$X$_y$ group, X denotes a residue of the formula

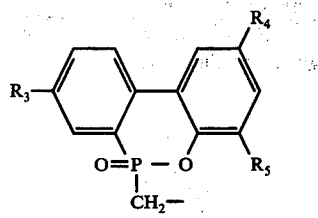

wherein R$_3$, R$_4$ and R$_5$ each denote a monofunctional residue selected from the class consisting of a hydrogen atom, a halogen atom, an alkyl having 1 to 8 carbon atoms, an aralkyl group, a cyclohexyl group and a phenyl group, x denotes an integer having the value of 1 or 2 and y denotes an integer having the value of 0, 1 or 2), said resin component comprising a graft copolymer and a styrenic polymer, said graft copolymer having polyphenylene ether in an amount of 20 to 80% by weight of the resin component and having 20 to 200 parts by weight of a styrenic compound or a combination of a styrenic compound and a vinyl compound copolymerizable therewith grafted onto 100 parts by weight of a polyphenylene ether represented by the generic formula:

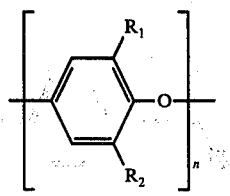

(wherein, R$_1$ and R$_2$ each denote an alkyl group having 1 to 4 carbon atoms and n denotes the degree of polymerization).

22. The resin composition according to claim 21, wherein the residue (C) is such that all $R_3$, $R_4$ and $R_5$ each are a hydrogen atom.

23. The resin composition according to claim 21, wherein the residue (C) is such that $R_4$ and $R_5$ each are a chlorine atom and $R_3$ is a hydrogen atom.

24. The resin composition according to claim 21, wherein the residue (C) is such that $R_3$, $R_4$ and $R_5$ each are a t-butyl group.

25. The resin composition according to claim 21, wherein the residue (C) is such that $R_5$ is a phenyl group and $R_3$ and $R_4$ each are a hydrogen atom.

26. The resin composition according to claim 21, wherein the residue (C) is such that $R_3$ and $R_5$ each are a methyl group and $R_4$ is a t-butyl group.

27. The resin composition according to claim 21, wherein the organic phosphorus compound (B) is such that Ar is a group of the formula

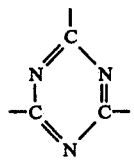

and Z and Z' each are a $-NH_{2-y}X_y$ group.

28. The resin composition according to claim 21, wherein the organic phosphorus compound (B) is such that Ar is a group of the formula

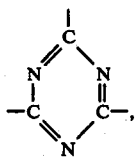

Z is a phenyl group and Z' is a $-NH_{2-y}X_y$ group.

29. The resin composition according to claim 21, wherein the organic phosphorus compound (B) is such that Ar is a

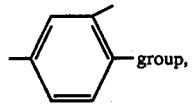

Z is a hydrogen atom and Z' is a $-NH_{2-y}X_y$ group.

30. The resin composition according to claim 21, wherein the organic phosphorus compound (B) is such that Ar is a

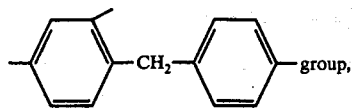

Z is a hydrogen atom and Z' is a $-NH_{2-y}X_y$ group.

31. The resin composition according to claim 21, wherein the organic phosphorus compound (B) is such that Ar is a

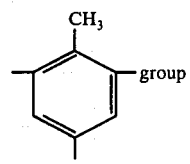

and Z and Z' each are a $-NH_{2-y}X_y$ group.

32. The resin composition according to claim 21, wherein the organic phosphorus compound (B) is such that Ar is a

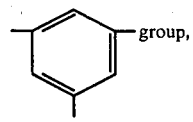

Z is a phenyl group and Z' is a $-NH_{2-y}X_y$ group.

33. The resin composition according to claim 21, wherein the organic phosphorus compound (B) is such that Ar is a

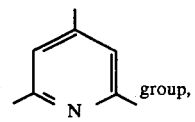

Z is a methyl group and Z' is a $-NH_{2-y}X_y$ group.

34. The resin composition according to claim 21, wherein the organic phosphorus compound (B) is such that Ar is a Z is a hydrogen atom and Z' is a $-NH_{2-y}X_y$ group.

35. The resin composition according to claim 21, wherein the organic phosphorus compound (B) is such that Ar is a

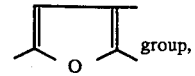

Z is a hydrogen atom and Z' is a $-NH_{2-y}X_y$ group.

36. The resin composition according to claim 21, wherein the organic phosphorus compound (B) is such that Ar is a

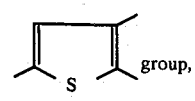

Z is a hydrogen atom and Z' is a $-NH_{2-y}X_y$ group.

37. The resin composition according to claim 21, wherein the organic phosphorus compound (B) is such that Ar is a

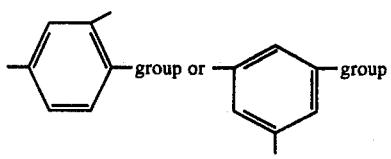

and Z and Z' each are a phenyl group.

38. The resin composition according to claim 21, wherein the organic phosphorus compound (B) is such that Ar is a

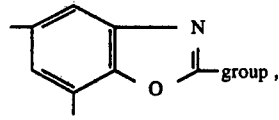

Z is a phenyl group and Z' is a $-NH_{2-y}X_y$ group.

39. The resin composition according to claim 21, wherein the organic phosphorus compound to be used is a mixture consisting of organic phosphorus compounds of the formula (B) wherein $x$ is 1 or 2 and $y$ is 0, 1 or 2.

40. The resin composition according to claim 1, wherein the polyphenylene ether (A) is such that $R_1$ and $R_2$ each are a methyl group.

* * * * *